United States Patent [19]

Umezawa et al.

[11] Patent Number: 4,592,999

[45] Date of Patent: Jun. 3, 1986

[54] PROCESS FOR PRODUCING DAUNOMYCIN

[75] Inventors: Hamao Umezawa; Tomio Takeuchi; Kageaki Kouno, all of Tokyo; Tomoyuki Ishikura, Chigasaki; Akihiro Yoshimoto, Fujisawa; Yukio Takatsuki, Yokohama; Hiroyasu Tobe, Tokyo, all of Japan

[73] Assignee: Sanraku Incorporated, Tokyo, Japan

[21] Appl. No.: 514,678

[22] Filed: Jul. 18, 1983

[30] Foreign Application Priority Data

Jul. 24, 1982 [JP] Japan ................................. 57-129370

[51] Int. Cl.⁴ .......................... C12P 19/56; C12R 1/34

[52] U.S. Cl. ....................................... 435/78; 435/886
[58] Field of Search ........................................... 435/78

[56] References Cited

U.S. PATENT DOCUMENTS 3,989,598  11/1976  Pinnert et al. ......................... 435/78
4,147,778   4/1979  Umezawa et al. ..................... 435/78

Primary Examiner—Alvin E. Tanenholtz
Attorney, Agent, or Firm—James J. Ralabate

[57] ABSTRACT

This invention is to provide a new microbial process for producing daunomycin by a mutant strain belonging to the genus Streptomyces.

1 Claim, No Drawings

PROCESS FOR PRODUCING DAUNOMYCIN

BACKGROUND OF THE INVENTION (1) Field of the Invention

The present invention relates to a process for producing daunomycin, and more particularly, to a microbial process for producing daunomycin having the general formula (I)

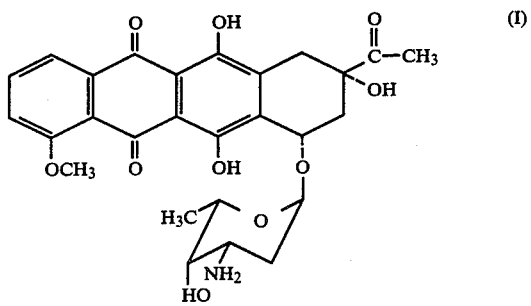

by culturing in a nutrient medium a mutant strain belonging to the genus Streptomyces capable of producing daunomycin and incapable of producing daunomycin analogues, said mutant strain being derived from strains belonging to the genus Streptomyces capable of producing daunomycin and analogues thereof simultaneously, and recovering daunomycin thus produced therefrom.

(2) Description of the Prior Art

A number of anthracycline glycosides have been described in prior literature. Among them, daunomycin is particularly being watched with keen interest by those in the field of cancer chemotherapy and has already been applied clinically for human cancers. Preparation of daunomycin by fermentation of *Streptomyces peucetius* N.C. I.B. 9475, of *Streptomyces griseus* var. *rubidofaciens* DS 32041, and of *Streptomyces bifurcus* DS 23219 is disclosed in U.S. Pat. No. 4,012,284. Chemical conversion of antibiotics complex produced by fermentation of *Streptomyces coeruleorubidus* NRRL 3045 and 3046 to daunomycin is disclosed in U.S. Pat. No. 3,989,598. However, as reported in J. Antibiotics 30, 619–621, 622–624, 1977 of the baumycins production by fermentation of *Streptomyces coeruleorubidus* ME 130-A4 which is known as a daunomycin-producing strain, the daunomycin-producing strains disclosed in said publications produce and accumulate in the broth as the final products daunomycin and analogues thereof simultaneously so that the recovery of daunomycin from the cultured broth needs a process of hydrolysis of daunomycin analogues to daunomycin by acidic treatment.

In the continuation of studies on fermentative production of daunomycin, the present inventors obtained a mutant strain which is capable of producing daunomycin and incapable of producing daunomycin analogues, from a daunomycin and baumycin-producing strain, *Streptomyces coeruleorubidus* ME 130-A4 (FERM P-3540), and succeeded in direct fermentative production of daunomycin without any process of acidic hydrolysis of daunomycin analogues.

OBJECTS OF THE INVENTION

Accordingly, it is an object of this invention to provide a new microbial process for producing daunomycin by fermentation.

DETAILED DESCRIPTION OF THE INVENTION

This invention relates to a novel process for the production of an anticancer antibiotic called daunomycin (also called daunorubicin) and more particularly, it provides a process for the production of daunomycin which is characterized by culturing in a nutrient medium a mutant strain belonging to the genus Streptomyces capable of producing daunomycin and incapable of producing daunomycin analogues, said mutant strain being derived from a strain belonging to the genus Streptomyces capable of simultaneously producing daunomycin and analogues thereof, and recovering daunomycin from said culture.

Daunomycin of the following formula:

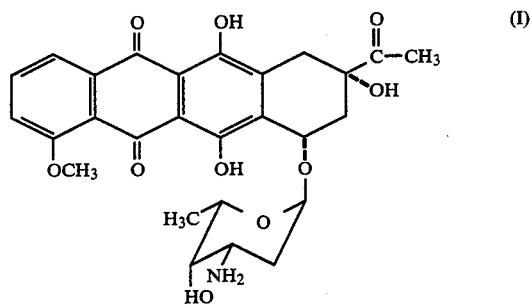

belongs to anthracycline type antibiotics and is one of carcinochemotherapeutically important clinical carcinostatic agents and, in particular, is an essential drug for the treatment of acute leukemia.

However, as described above, as made clear by the production of baumycins by a strain ME 130-A4, one of *Streptomyces coeruleorubidus* which has been recognized as a daunomycin producing bacterium (J. Antibiotics, 30, 619–621, 622–624, 1977), the daunomycin producing bacterium described in the aforesaid patent lieterature inherently has a nature of producing and accumulating daunomycin as the final product in the fermentation broth and at the same time producing and accumulating a baumycin of the following formula:

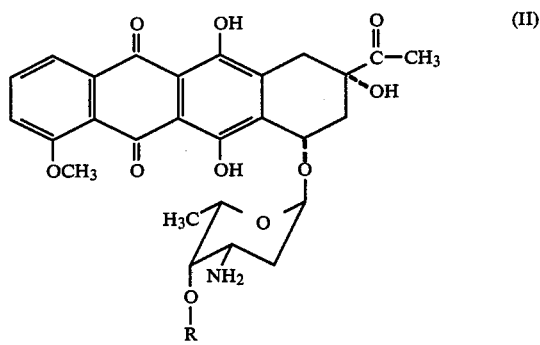

wherein R represents a group

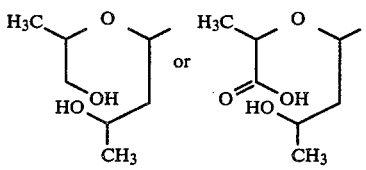

wherein a neutral sugar substance is further attached to the daunosamine C-4' position of daunomycin. Therefore, in order to efficiently recover daunomycin from the fermentation broth, it is necessary to liberate the neutral sugar attached to the C-4' position to convert to daunomycin by extracting the fermentation broth at a strong acidity (pH 2.0 or less) or further subjecting it to the heat treatment (for example, see U.S. Pat. No. 3,989,598). This is a fundamental operation which has been described in any of the aforesaid patent literature. In addition, the modification of the daunosamine C-4' position by the neutral sugar same as that attached to baumycin has also been proven using a carminomycin producing strain (J. Antibiotics, 27, 254, 34, 774), and thus this can be said a characteristic common to the anthracycline antibiotic producing strains belonging to the same class, such as daunomycin, carminomycin etc.

The present inventors have previously made clear that baumycins may be biosynthesized from daunomycin (e.g. J. Antibiotics, 33, 1158) and, based on this discovery, have intensively studied on the basis of the idea that by selecting and isolating one point of the biosynthesis route, that is, a mutant strain lacking the enzymatic reaction to attach a neutral sugar to daunomycin, daunomycin may be accumulated and recovered as the final product without producing daunomycin analogues, and as a result, have been successful in the isolation of the intended mutant strain which has been modified so as not to produce baumycin but to produce daunomycin which is a precursor thereto by the mutation treatment of a strain producing daunomycin and baumycin, i.e. Streptomyces coeruleorubidus ME130-A4 (FERM-P 3540 and ATCC 31276).

The isolation of a mutant strain having properties as those of the present strain has not yet been reported and this has now been achieved by the present inventors for the first time. In the present specification, the term "analogues of daunomycin" is employed as a generic name covering the aforesaid baumycin type antibiotics, 13213 R.P. substance (the aforesaid U.S. Pat. No. 3,989,598) etc.

Thus, according to the present invention, examples of the microorganism which can simultaneously produce daunomycin and analogues thereof include the aforesaid Streptomyces 8899, Streptomyces peucetius, Streptomyces griseus variety rubidofaciens DS 32041, Streptomyces bifurcus DS 23219, Streptomyces coeruleorubidus ME130-A4 and mutant strains thereof, but in addition to these strains, any microorganism belonging to thwe genus Streptomyces which can simultaneously produce daunomycin and its analogues may also be employed as a parent strain for a mutant strain capable of producing daunomycin and incapable of producing daunomycin analogues. Among the above, those which may be suitably employed in this invention include Streptomyces coeruleorubidus ME130-A4 (FERM-P 3540 and ATCC 31276) and Streptomyces 8899 (NRRL 3046) which is analogous to the former.

Further, while examples of the mutant strain capable of producing daunomycin and incapable of producing daunomycin analogues include all strains which have been obtained by the mutation of strains capable of simultaneously producing daunomycin and analogues thereof, said strains being derived from strains belonging to the genus Streptomyces, Streptomyces coeruleorubidus ME130-A4 strain may be mentioned as suitable.

In order to isolate the mutant strain suitable for the purpose of this invention, the aforesaid strain which is known to simultaneously produce daunomycin and daunomycin analogues may be subjected to the conventional mutation treatment which is known per se. One example is as follows: Streptomyces coeruleorubidus ME130-A4 strain is inoculated to a slope of YS agar (0.3% yeast extract, 1% soluble starch, 1.5% agar, pH 7.2) and cultured at 28° C. for a week. The deposited spores are collected by scraping, taken into 5 ml of an aseptic 0.1M Tris-HCl buffer (pH 8.5 containing 1 mM EDTA), then subjected to the ultrasonic treatment (15 seconds on a Ultrasonic Disruptor, Model UR-200P, Tomy Seiko), and passed through a small glass tube packed with sterilized absorbent cotton ($\phi 1.2 \times 2.0$ cm) to obtain 4.5 ml of an almost pure uniform spore solution. 0.5 ml of an aqueous solution of N-methyl-N'-nitro-N-nitrosoguanidine (NTG) of a concentration of 10 mg/ml is added thereto to effect the mutation treatment at 28° C. for 60 minutes while shaking slowly. The killing rate at that time was 92.6%. After the treatment, it is diluted appropriately with sterilized physiological saline, then 0.1 ml thereof is coated on a Petri dish plate obtained by plating and solidifying the YS agar (ditto) and cultured at 28° C. for 5 days. The produced colonies are isolated into the YS agar slope (ditto) and cultured, and the daunomycin producing capability is tested by the procedures described below.

Firstly, one platinum loop of the above isolated strain is inoculated to a test tube to which 4 ml of the seed culture medium set forth below has been added and sterilized, and reciprocatingly shake cultured at 28° C. for 2 days.

Medium for Seed Culture

| | |
|---|---|
| Soluble starch | 0.5% |
| Glucose | 0.5% |
| Essan Meat (soybean meal produced by Ajinomoto Co., Inc.) | 1.0% |
| Yeast extract | 0.1% |
| NaCl | 0.1% |
| $K_2HPO_4$ | 0.1% |
| $MgSO_4.7H_2O$ | 0.1% |
| Tap water | pH 7.4 |

Thereafter, the total volume is inoculated to a 250 ml Erlenmeyer flask to which 20 ml of the main culture medium set forth below has been added and sterilized, and shake cultured on a rotary shaker at 28° C. for 7 days.

Medium for Main Culture

| | |
|---|---|
| Taiwan yeast | 5% |
| Yeast extract | 0.3% |
| Soluble starch | 7.5% |
| NaCl | 0.2% |
| $CaCO_3$ | 0.3% |
| Minerals* | 0.125% |

| -continued | |
|---|---|
| Tap water | pH 8.0 |

*That obtained by dissolving 2.8 g of $CuSO_4.5H_2O$, 0.4 g of $FeSO_4.7H_2O$, 3.2 g of $MnCl_2.4H_2O$ and 0.8 g of $ZnSO_4.7H_2O$ in 500 ml of distilled water.

One ml of the broth is sampled from each culture flask, 2 ml of acetone is added thereto and stirred on a thermomixer, after which the product is extracted into the liquor layer. The supernatant and the mycrobial cells are separated by centrifugation, and 20 μl portions of the respective supernatant fractions are spotted on a silica gel thin layer ($F_{254}$, produced by Merck Co.) at positions 2 cm from the lower end and at 1 cm intervals, developed with chloroform/methanol/water/acetic acid (80/20/2/0.2) and compared with the daunomycin standard product. While the parent strain and most of the mutation treated ones give a number of reddish orange spots comprising baumycins ($A_1$, $A_2$, $B_1$, $B_2$ etc.) and aglycones, with the daunomycin producing mutant strain of this invention, a spot of very little dihyrodaunomycin is slightly observed but spots of anthracycline glycoside other than daunomycin are not detected.

By the above described procedures, the mutant strain suitable for the purpose of this invention was obtained in a proportion of about one out of 5000 strains of the mutation treated colonies.

The mycological properties of Streptomyces coeruleorubidus 3T-373 strain which is one of the strains thus obtained are shown below.

1. Morphology

The 3T-373 strain forms linear or hooked aerial hyphae and does not show whirls. The mature spore chains are 10 or more in number, and the size of the spores is about 0.4–0.8 × 1.2–2.0 microns, the surface of the spores being almost flat. Sometimes, protrusions similar to traces of stab protrusions are slightly observed on a part of the spores.

2. Growing Conditions in Various Media (1) Sucrose-nitrate agar medium (culture at 28° C.)
Deposits gray yellowish pink (5cb) aerial hyphae on the growth of light orange or dark orange to light brown (4ea-4gc) and the production of soluble dyes is hardly observed.

(2) Glucose-asparagine agar medium (culture at 28° C.)
Deposits a growth of grayish yellow or light orange yellow to light orange (3ec-3ea-4-ea). Hardly forms aerial hyphae and also hardly produces soluble dyes.

(3) Glycerin-asparagine agar medium (ISP-Medium 5, 28° C.)
Deposits gray yellowish pink (5cb) aerial hyphae on the growth of light orange (4ea) or orange to dark orange, and the soluble dyes are slightly tinged with orange.

(4) Inorganic salt-starch agar medium (ISP-Medium 4, 28° C.)
Deposits gray yellowish pink (5cb) aerial hyphae on the growth of light orange yellow or light orange (3ea-4ea) to reddish orange, and the soluble dyes are tinged with pink or slight pink.

(5) Tyrosine agar medium (ISP-Medium 7, 28° C.)
Deposits a purple-tinged white (13ba) to gray yellowish pink (5cb) aerial hyphae on the growth of light orange (4ea) or yellowish brown to reddish orange, and soluble dyes are hardly observed. When the culture is extended (for about 20 days), is tinged with red.

(6) Nutrient agar medium (culture at 28° C.)
Deposits gray yellowish pink (5cb) to extremely light purple (11ca) aerial hyphae on the growth of red to dark red.

(7) Yeast malt agar medium (ISP-Medium 2, 28° C.)
Deposits gray yellowish pink (5cb) aerial hyphae on the growth of dark orange (4gc) or yellowish brown to reddish brown, slight at the start and then abundantly from about the 14th day after the start of culture, and the soluble dyes are slightly tinged with orange.

(8) Oatmeal agar medium (ISP-Medium, 28° C.)
Deposits gray yellowish pink (5cb) aerial hyphae on the growth of light reddish brown (5gc) or reddish brown to brown, and the soluble dyes are extremely slightly tinged with pink.

(9) Glucose-peptone-gelatin medium (culture at 20° C.)
Slightly deposits thin and white aerial hyphae on the growth of yellowish brown to dark brown, and the soluble dyes slightly exhibit a brown color.

(10) Defatted milk medium (28° C.)
Grows on the surface, and the casein does not coagulate but partially peptonizes. The soluble dyes exhibit a brown tincture.

3. Physiological Properties (1) Growth temperature range
As the result of the test at temperatures of 20° C., 25° C., 30° C., 37° C., 46° C. and 50° C. respectively, growth was possible at any temperature except 46° C. and 50° C., but the optimum temperature seems to be in the vicinity of 30° C.–37° C.

(2) Liquefication of gelatin (glucose-peptone-gelatin medium, culture at 20° C., 20 days)
Liquefies.

(3) Hydrolysis of starch (inorganic salt-starch agar medium, culture at 28° C.)
Hydrolyzes starch.

(4) Coagulation and peptonization of defatted milk (defatted milk medium, culture at 28° C.)
Hardly coagulates but peptonizes.

(5) Formation of melanin-like dyes (tryptone-yeast-broth, ISP-Medium 1; peptone-yeast-iron agar, ISP-Medium 6; tyrosine-agar, ISP-Medium 7; culture at 28° C. respectively)
In the tyrosine-agar medium, melanin-like dyes are hardly formed or, even when formed, only a trace is observed. However, with the other two media, the formation of melanin-like dyes is clearly observed.

(6) Assimilability of carbon sources (Pridham-Gottlieb agar meidum, ISP-Medium 9, culture at 28° C.)
Assimilates L-arabinose, D-xylose, D-glucose, D-frustose, sucrose, inositol and D-mannite and grows well. Assimilation of L-rhamnose and raffinose is slight and doubtful.

The present strain was internationally deposited as FERM BP-165 (Streptomyces coeruleorubidus 3T-373) with the Fermentation Research Institute, Agency of Industrial Science and Technology, Japan as of July 13, 1982.

The production of daunomycin in accordance with this invention may be achieved by inoculating a mutant strain capable of producing daunomycin and incapable of producing daunomycin analogues, the strain being derived from a strain belonging to the genus Streptomyces capable of simultaneously producing daunomycin and analogues thereof, for example, spores or hyphae of the aforesaid *Streptomyces coeruleorubidus* 3T-373 to a medium containing nutrient sources and proliferating is aerobically.

The nutrient sources therefor are those conventionally employed as the nutrient sources for actinomyces, for example, as the carbon source, glucose, glycerin, sucrose, starch, maltose, animal and vegetable oils may be employed, and as the nitrogen source, for example, organics such as soybean meal, meat extract, yeast extract, peptone, corn steep liquor, cotton seedcake etc. and inorganic nitrogens such as ammonium sulfate, ammonium chloride, ammonium nitrate, ammonium phosphate etc. may be employed. Further, according to the necessity, in addition to add inorganic salts such as table salt, potassium chloride, phosphates and other heavy metal salts etc. and vitamins, it is also possible to appropriately add a defoamer such as Silicone (KM 75, trademark, produced by Shinetsu Chemical Industry Co., Ltd.) etc.

The fermentation conditions such as the temperature, pH, aerobic stirring and fermentation time are selected so that the strain used can accumulate the maximum amount of said compound. For example, as the fermentation conditions, it is advantageous to conduct it at a temperature of 20° C.–40° C., preferably 28° C., at a pH of 5–9, preferably 7.4, for 1–5 days, preferably 3 days.

In order to isolate daunomycin from the fermentation culture, the microbial cells and the filtrate are separated by the conventional means in the art of the production of anthracycline antibiotics, for example, by centrifugation or filtering the culture liquor in the presence of a suitable filtering aid such as diatomite, and thereafter it may be extracted from the microbial cells with an organic solvent miscible with water such as acetone, methanol, ethanol, butanol etc. and from the filtrate with an organic solvent such as chloroform, ethyl acetate, but it is also possible to directly extract from the culture without previous separation by appropriately selecting these solvents.

In order to isolate the intended product, gel chromatography using silica gel etc., gel permeation using Sephadex LH-20 (produced by Pharmacia Co.), Bio-Gel P-2 (produced by Bio Rad Co.) etc., adsorption and elution using methacryl or acryl type weakly acidic cation exchange resins etc. are employed either singly or in appropriate combination or even sometimes repeatedly.

Further, as described above, on recovering daunomycin from the daunomycin containing culture, it has previously been necessary to conduct the treatment for converting daunomycin analogues to daunomycin and subsequently conduct the aforesaid recovering means in order to obtain daunomycin in a high yield, but according to this invention, since not only such treatment is no longer particularly needed but also the aforesaid chromatography treatment etc. may be easily carried out, daunomycin may be recovered and isolated in a high yield.

This invention is more particularly described by the following examples.

EXAMPLE 1

One platinum loop was taken from an YS slope culture of *Streptomyces coeruleorubidus* 3T-373 strain, inoculated to a 500 ml Erlenmeyer flask to which 100 ml of the seed culture medium described below had been added and sterilized, and shake cultured on a rotary shaker (220 rpm) at 28° C. for 2 days to prepare a seed culture.

Seed Culture Medium

| | |
|---|---|
| Soluble starch | 0.5% |
| Glucose | 0.5% |
| Essan Meat (soybean meal produced by Ajinomoto Co., Ltd.) | 1.0% |
| Yeast extract | 0.1% |
| NaCl | 0.1% |
| K$_2$HPO$_4$ | 0.1% |
| MgSO$_4$.7H$_2$O | 0.1% |
| Tap water | pH 7.4 (before sterilization) |

Thereafter, the above-described seed culture was added and inoculated to two 30 liter jar fermenters to which 15 liters of the production medium having the following composition has been added and sterilized, in a rate of 750 ml per fermenter (corresponding to 5%).

Production Medium

| | |
|---|---|
| Taiwan yeast | 5% |
| Soluble starch | 7.5% |
| Yeast extract | 0.3% |
| NaCl | 0.2% |
| CaCO$_3$ | 0.3% |
| Mineral mixed solution* | 0.125% |
| Tap water | pH 8.0 (before sterilization by heating) |

*that obtained by dissolving 2.8 g of CuSO$_4$.5H$_2$O, 0.4 g of FeSO$_4$.7H$_2$O, 3.2 g of MnCl$_2$.4H$_2$O and 0.8 g of ZnSO$_4$.7H$_2$O in 500 ml of distilled water.

When culture was carried out at an aeration rate of 5 l/m and stirring of 450 rpm at 28° C. for 120 hours, the culture liquor exhibited a deep reddish brown color, and daunomycin accumulated in an amount of about 380 μg per ml of the culture liquor. The quantitative analysis of daunomycin was carried out as follows: The daunomycin extract was suitably diluted then 10–20 μl thereof was spotted at a position 2 cm from the lower end of a thin layer silica gel plate (F$_{254}$ produced by Merck Co.), developed with chloroform/methanol/water/acetic acid (80/20/2/0.2), the daunomycin spot was measured using a thin layer chromatoscanner (Model CS-910, produced by Shimazu Seisakusho) and assayed by calculating based on the standard curve.

After 120 hours of culture, the fermentation was ceased, the culture liquors were collected from the two jar fermenters (27 liters in total volume) and separated into the microbial cells and the filtrate by centrifugation. Daunomycin in the filtrate was extracted with a total volume of 10 liters of chloroform. On the other hand, daunomycin in the microbial cell fraction was extracted with a total volume of 8 liters of acetone, and the extract supernatant was concentrated under reduced pressure to about ⅓ in volume. Thereafter, it was extracted with 2 liters of chloroform twice. They were combined with the aforesaid chloroform extract from the filtrate and concentrated to dryness to obtain 8.47 g of a crude daunomycin standard product of a purity of about 50%.

EXAMPLE 2

The total amount of the crude standard product obtained in Example 1 was suspended or dissolved in 0.1M acetic acid (pH 3.0), and the insolubles were removed by filtration. The supernatant was neutralized with a 4N caustic soda solution to adjust the pH to 8.0, and extracted again with chloroform. The chloroform extract was washed with water, dried on Glauber's salt, then concentrated to a small volume, and an excess of n-hexane was added thereto to cause precipitates, which were collected by filtration and dried in vacuum to obtain 4.57 g of a reddish brown daunomycin powder having a purity of about 85%.

Thereafter, the total amount of this daunomycin powder was dissolved in 300 ml of chloroform, 20 g of silica gel (Art. 7734 produced by Merck Co.) was added thereto and mixed to adsorb it followed by concentration under reduced pressure to dryness. This was placed on a column ($\phi 5.2 \times 16$ cm) packed with 150 g of the same silica gel suspended in chloroform, and developed and eluted with 5 liters of chloroform/methanol/water (15/2/0.2). The daunomycin eluate fractions were collected, washed with water, dried by adding Glauber's salt, and concentrated to dryness to obtain 3.31 g of a reddish brown powder of daunomycin of a purity of 98.5%.

What is claimed is:

1. A process for producing daunomycin which comprises culturing in a nutrient medium a mutant strain capable of producing daunomycin and incapable of producing daunomycin analogues, said mutant strain being derived from strains capable of producing daunomycin and daunomycin analogues simultaneously wherein said mutant strain is *Streptomyces coeruleorubidus* 3T-373, and recovering daunomycin thus produced from the broth.

* * * * *